United States Patent [19]

Carr

[11] 4,080,076

[45] Mar. 21, 1978

[54] SUSPENDED SOLIDS ANALYZER USING MULTIPLE LIGHT SOURCES AND PHOTODETECTORS

[75] Inventor: Larry R. Carr, West Chicago, Ill.

[73] Assignee: Optronix Inc., St. Charles, Ill.

[21] Appl. No.: 709,326

[22] Filed: Jul. 28, 1976

[51] Int. Cl.² .................................. G01N 21/26
[52] U.S. Cl. .................... 356/208; 250/565; 356/206
[58] Field of Search ............... 356/205, 206, 208; 250/564, 565

[56] References Cited

U.S. PATENT DOCUMENTS

| 3,146,293 | 8/1964 | Lesage | 356/205 |
| 3,652,850 | 3/1972 | Briggs | 356/208 |
| 3,659,943 | 5/1972 | Goolsby | 250/564 |
| 3,684,378 | 8/1972 | Lord | 356/205 |
| 3,955,096 | 5/1976 | Faulhaber | 356/205 |

Primary Examiner—John K. Corbin
Assistant Examiner—R. A. Rosenberger
Attorney, Agent, or Firm—Hill, Gross, Simpson, Van Santen, Steadman, Chiara & Simpson

[57] ABSTRACT

A method of analyzing suspended solids, particularly in flowing liquids, in which a plurality of light sources and photodetectors are employed in predetermined arrangement to provide a relatively short light path and a relatively long light path for each photodetector, with the light sources being actuated in predetermined off-on sequence, to provide corresponding periods of illumination from each light source and intermediate periods of no illumination, with the no illumination value representing ambient light, and so combining the respective light values so obtained to provide values representing not only the suspended solid content but also comparison values indicating the presence of failures of the respective light sources and photodetectors, and apparatus for practicing the method.

21 Claims, 6 Drawing Figures

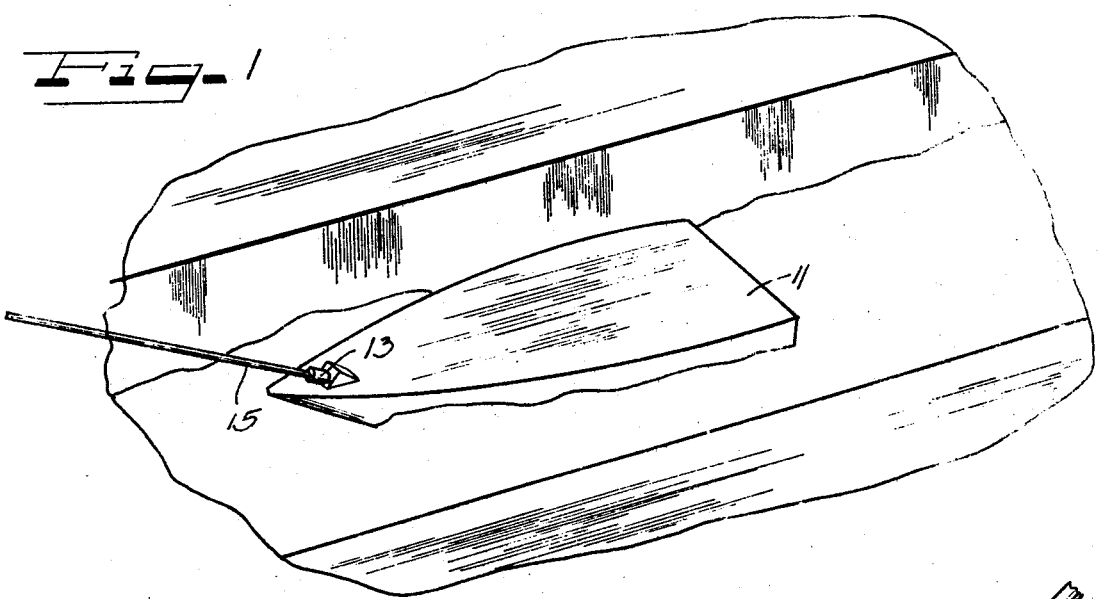
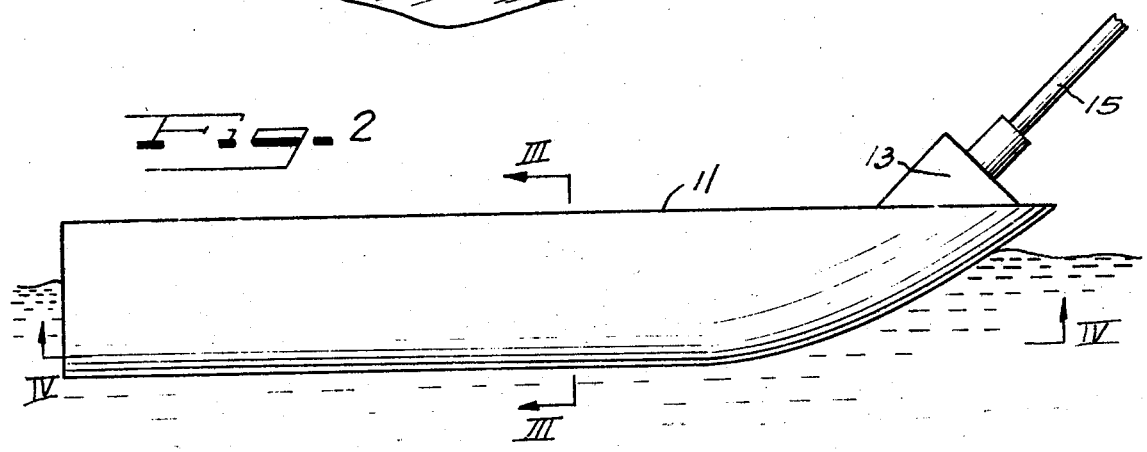
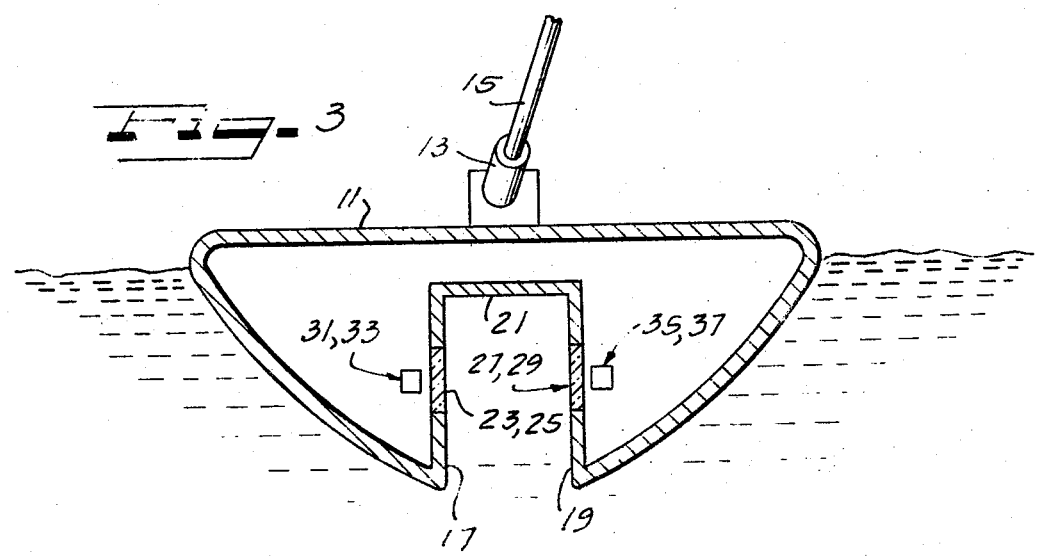

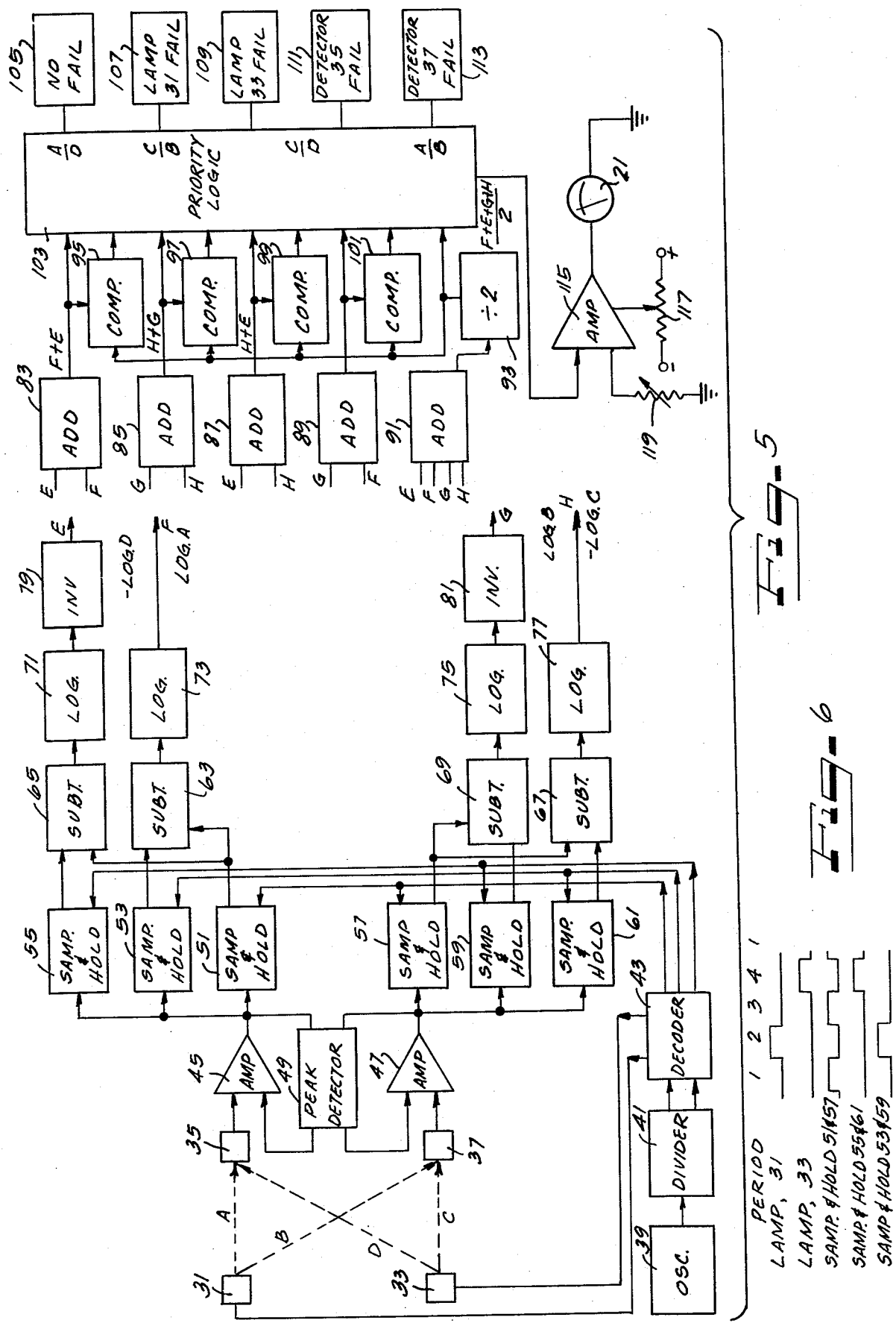

SUSPENDED SOLIDS ANALYZER USING MULTIPLE LIGHT SOURCES AND PHOTODETECTORS

BACKGROUND OF THE INVENTION

The invention relates to the automatic and continuous measurement of particles suspended in a liquid, and particularly to the measurement of liquids that flow in open channels or streams. This includes the effluents from waste treatment plants, settling tanks, ponds, streams, and lakes, and anywhere that low concentrations of solids are present along with adhesive scum, algae, and strong ambient light.

In such liquids it is desirable to measure the concentration of suspended solids continuously without disturbing the liquid to the extent that bottom sediment might be stirred up and mixed with an otherwise clear liquid or to the extent that delicate flocculated particles might be broken up or otherwide modified from their natural state prior to measurement. In addition, it is desirable to measure these relatively clear liquids without interference from ambient light (particularly sunlight) and without interference from scum or algea which can accumulate quite rapidly. These requirements inpose conflicting constraints on the design of an instrument and, up to the present time, no device has been available which satisfies all of them.

Furthermore, in the critical area of monitoring the effluents of municipal and industrial waste water treatment plants, any measurement errors or drift in calibration of a monitoring instrument have serious financial, legal, and environmental impacts which are so important that no prior instrument has been approved for continuous unattended monitoring. The problem here is not only that the instruments drift or change calibration, but that this drift goes on unnoted, and invalid measurements are indistinguishable from valid ones.

Aside from manual laboratory analysis, there are three methods that are suitable for measurement of suspended solids concentrations in relatively clear liquids: light scattering, light transmission, and a combination of the scattering and transmission. Methods that use light scattering either alone or in combination have high sensitivity but are subject to uneven response due to the widely varying scattering coefficients of many types of solids; they therefore are used successfully only in processes which have a singular type of solids. Light transmission instruments overcome this problem, but they have inherently lower sensitivity in low concentrations, unless very long light paths are used. Both types are affected by the presence of ambient light; in scattering instruments ambient light tends to give the same indication as an increase in solids concentration, and in transmission instruments ambient light produces the same indication as a decrease in solids concentration. Both types employ light shields or baffles to reduce ambient light, but since sunlight may be hundreds of times stronger than the instrument's light source, the shielding must be extremely effective, and most designs mount the optical detector in a pipeline, fed by a pump. The pipeline presents a tortuous path that greatly attenuates ambient light, but it also restricts the flow of the liquid. A pump then becomes necessary not only to guarantee that a constantly fresh sample is being measured, but also to provide some high velocity cleansing action to the measurement surfaces so that scum and algae do not build up and provide their own interference to the measurement (scum and algae both absorb and scatter light.) The pump and pipeline, no matter how small, tend to break up particles (particularly flocculated particles) into smaller particles, which in turn means that the character of the measured liquid is significantly altered from its original state. A pump also is an additional maintenance problem, since it can fail or clog with debris.

BRIEF SUMMARY OF THE INVENTION

The invention overcomes these objectional features and provides a new and novel method for measuring suspended solids without the traditional problems associated with this measurement, and additionally providing new and important information on the condition of the measurement accuracy at the same time. These results are achieved by a new and novel technique using multiple light sources and photodetectors.

Accordingly, an object of the invention is to provide a measurement of low values of suspended solids in the presence of high values of ambient light.

Another object of the invention is to provide a measurement of suspended solids in quiescent liquids without disturbing the liquids.

Still another object of the invention is to provide a measurement of suspended solids without interference from scum and algae growth.

A further object of the invention is to provide a measurement of suspended solids without changing the character of the solids due to violent movement or agitation.

Additionally, an object of the invention is to provide a measurement of suspended solids whose accuracy is assured by a continuous self-checking circuit.

Still another object of the invention is to provide a continuous monitor of suspended solids concentration which signals its own condition and warns of required maintenance prior to any failure.

These objectives are achieved in the invention by the utilization of a method of analyzing suspended solids in a liquid, in which the liquid to be analyzed is traversed by light beams from a pair of light sources, each of which transmits light to each of a pair of light detectors, with light from one source being transmitted over a relatively short path to one of the detectors and over a relatively long path to the second of such detectors and light from the other source being transmitted to the first detector over a relatively long path and to the second detector over a relatively short path. The respective short paths are equal, and the respective long paths are likewise equal with each photodetector thus receiving light from each light source, one over a relatively short path and the other over a relatively long path. The respective light sources are alternately actuated at spaced time intervals with the intermediate periods therebetween having neither source actuated and thus representing ambient light values. The results of one complete sampling cycle, represented by two dark intervals and one actuation of each light source, are stored, for each photodetector, and after subtraction of the ambient values from the respective light values, and a logarithm conversion, the log values of the short light paths and the log values of the long light paths, in inverted form, are suitably combined in various combinations, whereby failure in any lamp or detector may be readily ascertained in correspondence to a monitoring of the respective combination values, for example utilizing a comparison operative between the various combinations. The geometric means may form the measurement output.

In practice of the method of the invention means such as a float assembly may be employed, disposed in the liquid to be analyzed and provided with an inverted channel extending longitudinally therealong, with two light sources and two photodetectors being disposed at opposite sides of the channel and arranged to provide a light path from each light source to each of the photodetectors, thereby forming a relatively short light path and a relatively long light path from each light source whereby each photodetector receives light from one light source over a short path and light from the other light source over a relatively long path, with the corresponding short paths being equal in length and corresponding long paths being equal in length.

Control means is provided for alternately actuating each of the light sources, with intermediate periods of no actuation of either light source representing ambient light values. The received light values at the respective photodetectors, following suitable amplification, are sampled and stored in respective sampling and holding or storing devices whereby the respective ambient and long and short light values may be derived, and following subtraction of the ambient light value from the respective source values, values representing the transmitting light from the respective sources may be derived. These values may be converted into logarithmic values and by suitable comparisons between predetermined combinations, employing the respective light values, with the geometric mean of all four values as well as with various combinations of each other, not only can an accurate determination of the suspended solids be achieved, but also actuation of indicating or alarm means may also be effected to indicate the proper operation of the circuits, the failure of either lamp or the failure of either detector, as well as provide an indication of the condition of any windows utilized through which the light beams pass and thus indicate the presence of scum and algae thereon.

BRIEF DESCRIPTION OF THE DRAWINGS

In the drawings, wherein like reference characters indicate like or corresponding parts:

FIG. 1 is a perspective view of a typical flow installation embodying the present invention;

FIG. 2 is a side elevational view of the flow assembly illustrated in FIG. 1;

FIG. 3 is a transverse sectional view taken approximately on the line III—III of FIG. 2;

FIG. 5 is a schematic circuit diagram of apparatus by means of which the invention may be practiced; and FIG. 6 is a chart illustrating the timing of the respective light sources and corresponding sampling and holding circuits.

DETAILED DESCRIPTION OF A PREFERRED EMBODIMENT

Figure 4:
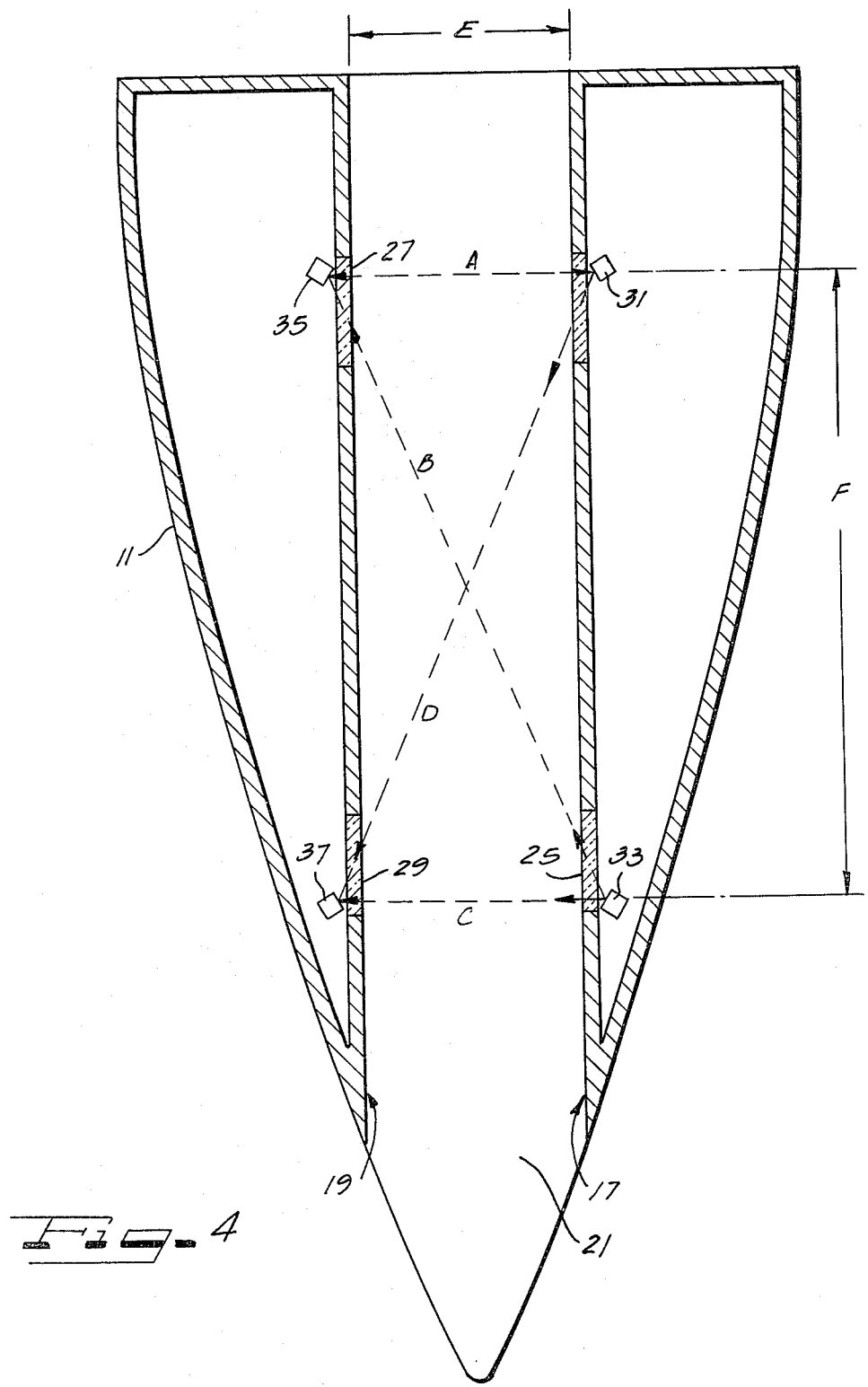
FIG. 4 is a longitudinal sectional view taken approximately on the line IV—IV of FIG. 2.

Referring to FIG. 1, the sensor assembly 11, is illustrated in a typical installation, floating in an open channel of liquid whose suspended solids concentration is to be measured. The sensor assembly 11, is bouyant and floats teathered by electrical connector 13, to cable 15. FIG. 2 shows a side view of the sensor assembly. FIG. 3 shows the sensor assembly vertical cross section taken along lines A-A in FIG. 2. The assembly is essentially shaped like a boat hull with a rectangular channel or notch extending longitudinally along the axis thereof, which opens on the bottom of the assembly, and is formed by a first vertical wall 17, a horizontal wall 21, and a second vertical wall 19. The first and second vertical walls 17 and 19 are flat and parallel to one another and to the longitudinal axis of the sensor assembly 11, and separated by a distance "E" (FIG. 4). A first window 23, and a second window 25, are mounted in the first vertical wall 17, at the same elevation, and separated horizontally by a distance "F", as shown in FIG. 4. A third window 27, and a fourth window 29, are in like manner mounted in the second, vertical wall 19, so that first window 23, is directly opposite the third window 27, and second window 25, is directly opposite the fourth window 29. These four windows form a rectangle in the horizontal plane so that the distance "A" from the first window 23, to the third window 27, is the same as the distance "C" from the second window 25, to the fourth window 29. Likewise the diagonal distance "B", from the third window 27, to the second window 25, is the same as the diagonal distance "D" from the first window 23, to the fourth window 29.

A first light source 31 is positioned behind the first window 23 so as to illuminate the third window 27, through the distance "A", and to also illuminate the fourth window 29, through the distance "D". A second light source 33 is positioned behind the second window 25 so as to illuminate the fourth window 29, through the distance "C", and to also illuminate the third window 27, through the distance "B". A first photodetector 35 is positioned behind the third window 27, so as to receive illumination from the first light source 31, through the distance "A", and also so as to receive illumination from the second light source 33, through the distance "B". A second photodetector 37 is positioned behind the fourth window 29 so as to receive illumination from the second light source 33, through the distance "C", and also so as to receive illumination from the first light source 31, through the distance "D".

Assuming for the moment that light sources 31 and 33 are of equal intensity, it can be seen that the amount of light reaching the first photodetector 35, through the distance "A", is equal to the amount of light reaching the second photodetector 37, through the distance "C". In similar fashion, the amount of light reaching the first photodetector 35, through the distance "B", is equal to the amount of light reaching the second photodetector 37, through the distance "D". It follows then that if first and second light sources 31 and 33 are alternately turned on and off, the two signals from first and second photodetectors 35 and 37 would alternate between weak and strong but would be equal to one another, and complementary in time; that is, the signal from each photodetector would be strongest when nearest light source was on, and weakest when the furthest light source was on, and the period having the strongest signal on either photodetector would correspond to the period having the weakest signal of the other photodetector.

In actual practice, the instantaneous total amount of light received by either photodetector is the sum of the illumination by the light source that is on and the amount of ambient light that reaches the photodetector. In order to use the amount of light that reaches the photodetector from either light source, the amount of ambient light must be compensated for. This is achieved in the invention by turning off both light sources for a short period and measuring the amount of ambient light that each photodetector receives. This amount is not only measured, but stored and the stored value is subsequently subtracted from the measured illumination when either light source is on. The subtraction process leaves a true value of the light passing from the light source to the photodetector, with ambient light effectively cancelled out.

The amount of light reaching either photodetector is dependent on several factors: the amount of ambient light (just mentioned, above) the strength of the light sources, the amount of attenuation through the windows, the amount of light attenuated by the liquid over a given distance, the amount of light attenuated by the solids in the liquid over a given distance, the sensitivity of the photodetectors, and the amount of attenuation on the window surfaces due to scum, debris, or algae growth. It is not safe to assume that the amount of attenuation due to scum and algae growth on the windows will be equal for each window, nor is it safe to assume that the two photodetector sensitivities or that the light source intensities will change from initial values at equal rates; i.e. they will all drift at unpredictable rates. The invention solves these problems as follows.

When light sources 31 and 33 are alternately turned on, the signal produced by the first photodetector 35 is directly proportional to the light absorption through the distances "A" and "B", the relative strengths of the two light sources, and the attenuation due to scum on the two windows 23 and 25. This signal is also proportional to the attenuation due to scum on the window 27, and its own sensitivity, but these latter two factors are the same no matter which light source is on, and they can be made to cancel out if the ratio of the amount of light when one source is on is taken to the amount of light when the other source is on (assuming that ambient light has previously been subtracted).

This ratio has the sensitivity and attenuation of one photodetector cancelled out, but it is still dependent on the relative strengths of the two light sources. While this measurement is being made, however, the second photodetector 37 is making an identical measurement, but due to the fact that the two signals are complementary the resulting two ratios are identical only when both light sources are equal, and they will depart from equality at equal rates (in opposite directions) as the strength of one light source is increased or decreased relative to the other light source. Their product, however, will remain constant since an increase in one will be exactly equalled by the decrease in the other, and their geometric mean (the square root of their product) will have the same value as either ratio would have had if the light source strengths has remained constant. This geometric mean, therefore, is a drift-free signal, since it is not dependent on the slime coating on any window, the relative strengths of either light source, or the sensitivity of either photodetector, and thus forms an ideal output measurement value.

This geometric mean may be simultaneously calculated in a manner that is similar to the first, but referenced differently: when either light source is on, both photodetectors receive light from it, one through a short distance ("A" or "C") and the other over a longer distance ("B" or "D"). If the ratio of these two signals is taken, it will contain as an interfering factor the relative sensitivities of the two photocells, but the absolute strength of the light source in question (and attenuation at its window) will be cancelled out. If, during the alternate time period, when the other light source is on, a similar ratio is taken, it will have the other light source factors cancelled out. Both will contain the photodetector factors, (as the previous method contained the light source factors), and in a similar manner their geometric mean will have all the factors cancelled out.

The two geometric means cited above are equal. They differ in the order in which the photodetector or light source errors were cancelled out, and although the final value is the same they have different intermediate values which are independently valuable in predicting a failure. These intermediate values are:

1. The ratio of the light from the first light source 31, to the light from the second light source 33, as measured by the first photodetector 35. This value will remain valid and equal to the geometric mean, even if the second photodetector drifts dramatically.
2. The ratio of the light from the second light source 33, to the light from the first light source 31, as measured by the second photodetector 37. This value will remain valid and equal to the geometric mean, even if the first photodetector drifts dramatically.
3. The ratio of the light reaching the first photodetector 35, to the light reaching the second photodetector 37, as illuminated by the first light source 31. This value will remain valid and equal to the geometric mean, even if the second light source 33 drifts dramatically.
4. The ratio of the light reaching the second photodetector 37, to the light reaching the first photodetector 35, as illuminated by the second light source 33. This value will remain valid and equal to the geometric mean, even if the first light source 31, drifts dramatically.

It will be noted that each of the above intermediate signals contain factors due to three of the four measuring elements, and its value will remain valid even if the fourth element fails utterly. In the case of an utter failure, the geometric mean no longer remains valid in all cases, and just prior to the failure the other three intermediate values depart significantly from the geometric mean. Use therefore can be made of this departure by means of automatic comparitor and switching circuits, which compare the four intermediate values with the geometric mean, and automatically switch the output indication from the geometric mean to the remaining valid signal (the one that has not departed significantly) whenever prescribed limits are exceeded. This same automatic switching circuit may initiate actuation of an alarm for the operator to signify that one of the measuring elements has failed, but that the measurement is still valid. Since most failures will be due to the presence of slime buildup on one of the windows, a simple cleaning can be done at once without any loss of service. This is particularly important in remote areas, where a simple trip by the operator when, and only when it is needed, can save hundreds of hours of incorrect data. In extremely critical applications, all four of the interim values can be recorded continuously to detect trends.

The actual suspended solids measurement is taken from the ratio of light passing through the liquid over two different distances. Suspended solids will absorb light through these two paths according to Beer-Lambert's Law, which states that the amount of light transmitted a given distance is inversely proportional to the logarithm of the concentration and the logarithm of the distance, or in the case of two different distances, the concentration is equal to the logarithm of the ratio of the two amounts of light transmission minus a constant. Since the present method already employs ratios, it becomes a simple matter to take the logarithm of the various signals and simply add or subtract them instead of utilizing electronic division or multiplication. Since the absolute values before logarithmic conversion are unimportant using this arrangement, the signals from the photodetectors can be processed through input amplifiers having variable amplification factors (AGC, or Automatic Gain Control) provided, of course, that all signals are amplified equally for a given set of conditions. This capability provides a very wide dynamic range which is necessary to handle the extremely wide amplitudes of ambient light that the detectors may sense, without saturating or otherwise distorting the signals. AGC may be provided through peak detectors which monitor the output at the input amplifiers.

A preferred embodiment is illustrated in FIG. 5. An oscillator 39, provides a continuous series of pulses to a divider 41, and decoder 43, which produces three output signals that divide the full measurement cycle into four periods, as illustrated in FIG. 6. During the first period both light sources are off, and each photodetector measures the ambient light. These signals are amplified by variable gain amplifiers 45 and 47 which are connected to photodetectors 35 and 37, respectively. A peak detector 49, measures the peak amplitude of the output signals of the amplifiers 45 and 47, and produces gain voltage that keeps the peak amplitude of the amplifiers at a constant value and within their linear region. The time constant of this circuit is, for example, about ten times the period of the oscillator 39 so that the gain is not varied significantly during any single measurement cycle. The output of the first variable gain amplifier 45 is connected to the input of three sample and hold amplifiers 51, 53 and 55. During the first period, a sample pulse is generated by the decoder and sent to the first sample and hold circuit 51, which causes it to store and hold the values of ambient light as sensed by the first photodetector 35. Similarly, the output of the second variable gain amplifier 47 is connected to the input of three sample and hold amplifiers 57, 59 and 61. The same sample pulse sent to the first sample and hold circuit 51 is likewise sent to the fourth sample and hold circuit 57, which causes it to store and hold the value of ambient light as sensed by the second photodetector 37.

During the second period, the decoder 43 produces a pulse that turns on the first light source 31 and causes the second sample and hold circuit 53 to store and hold the amount of light received by the first photodetector 35, while the first light source 31 is on. At the same time the fifth sample and hold circuit 59 is caused to store and hold the amount of light received by the second photodetector 37 while the first light source 31 is on.

The third period is identical to the first; both light sources are off and the first and fourth sample and hold circuits 51 and 57 update their ambient light measurements.

During the fourth period, the decoder 43 produces a pulse that turns on the second light source 33, and caused the third sample and hold circuit 55, to store and hold the amount of light received by the first photodetector 35, while the second light source 33 is on. At the same time the sixth sample and hold circuit 61 is caused to store and hold the amount of light received by the second photodetector 37, while the second light source 33 is on. The four periods then continuously sequentially repeat with the sample and hold circuits continually updating their information in a nearly constant manner.

The first subtractor 63 subtracts the stored ambient light value from the value stored in sample and hold circuit 53 and its output is directly proportional to the output of the first photodetector 35, as illuminated over the distance "A" by the first light source 31, and independent of the ambient light. The second subtractor 65 similarly produces an output directly proportional to the output of the first photodetector 35, as illuminated over the distance "D" by the second light source 33, and independent of ambient light. The third subtractor 67 similarly produces an output directly proportional to the output of the second photodetector 37 as illuminated over the distance "C" by the second light source 33 and independent of ambient light. The fourth subtractor 69 likewise produces an output directly proportional to the output of the second photodetector 37, as illuminated over the distance "B" by the first light source 31, and independent of ambient light.

The logarithms of these four signals are derived from four logarithmic converters 71, 73, 75 and 77. The outputs of logarithmic converters 71 and 75, which contain signals related to the longer light paths "B" and "D" are inverted by respective inverters 79 and 81, whereby these output signals are minus logarithms corresponding to division.

The four logarithmic signals are now variously combined in five adding circuits 83, 85, 87, 89 and 91. Each of the first four adds one positive logarithmic signal with one negative logarithmic signal, i.e., it subtracts one from the other. All of the results are the equivalent of the logarithm of the ratio of two values, and in each case the numerator is a measurement over the short distance (either "A" or "C") and the denominator is a measurement over the long distance (either "B" or "D"). These represent the four values previously described and each is directly proportional to the suspended solids concentration, less some constant. The fifth adding circuit 91 receives all four logarithmic signals and produces the composite value equal to twice the geometric mean cited earlier. This value is divided by two in the voltage divider 93, to produce a value equal to the geometric mean. This value is equal to each of the outputs of the first four adders 83, 85, 87 and 89 so long as none of the photodetectors, light sources or windows are defective.

The geometric mean voltage is compared with the output of these four voltages in comparitors 95, 97, 99 and 101 which are set to produce an error voltage whenever the comparison is off by some nominal value, for example 5%. As illustrated in FIG. 5, the comparison results along with the output results of the adders 83, 85, 87 and 89 and the geometric mean value of the divider 93 may be conducted to a priority logic circuit 103. Since a failure of any one element causes three of the four adding circuits 83, 85, 87 and 89 to drift from the geometric mean voltage at divider 93, a simple diode network (not illustrated) in the priority logic circuit 103 can be utilized to automatically switch the good signal to the output in place of the geometric mean and signal an alarm condition prior to a total failure. Five alarm output conditions are illustrated as examples, which are "no faults", "failure light source 31", "failure light source 33", "failure photodetector 35", and "failure photodetector 37", respectively designated by reference numerals 105, 107, 109, 111 and 113. Obviously many other alarm combinations are possible, particularly with timers, and automatic reset circuits.

An output amplifier 115 is used to scale the logarithmic signal up to standard signal transmission levels which, as previously pointed out, would normally be the geometric mean value. Its zero offset may be controlled by a potentiometer 117, and its gain controlled by a potentiometer 119. Suspended solids concentration thus may be read directly on meter 121.

Although the preferred embodiment is shown with common analog circuit elements for the sake of simplicity and clarity, persons skilled in the arts will readily appreciate that many digital computing and electromechanical techniques may be employed to achieve the same end without exceeding the spirit of the invention or the scope of the claims.

I claim as my invention:

1. A method of analyzing suspended solids in a liquid, particularly a flowing liquid, comprising the steps of traversing the liquid with light transmitted from two spaced locations and receiving light from each light transmitting location at two respective locations, with light being received at each receiving location from a respective transmitting location over a relatively short path and from the other transmitting location over a relatively long path, with the respective short paths being of equal length and the respective long paths being of equal length, transmitting light from said locations alternately with intermediate periods therebetween of no light transmission, with the latter periods representing ambient light values at the receiving locations, cyclically sampling light values at each receiving location for each light transmission thereto and the ambient light thereat, temporarily storing such values, subtracting the ambient light values received at a receiving location from the light values received thereat from the respective transmitting locations to form corrected light values from each transmitting location, forming therefrom the geometric mean of said corrected values as a measurement value of the suspended solids in said liquid, combining the four respective corrected light values in predetermined combinations and comparing the respective combinations with the geometric mean value to provide comparison results respectively indicative of failure of any of the respective light transmissions or receptions.

2. A method according to claim 1, wherein each value representing one of said four corrected light values is subjected to a logarithmic conversion and the log values utilized in the formation of said predetermined combinations.

3. A method according to claim 2, wherein said log values representing the long path light values are inverted prior to the formation of said predetermined combinations.

4. A method according to claim 3, wherein one of said predetermined combinations is derived from all four light values as the geometric mean.

5. A method according to claim 3, wherein said combinations comprise the ratios of each of the corrected short path values over each of the corrected long paths values, and the combination of the sum of all four of said corrected log and inverted log values divided by two.

6. A method according to claim 5, wherein the output measurment value normally is the geometric mean of the respective ratios.

7. A method according to claim 6, comprising the additional step of substituting for said geometric mean as the measurement value, in the event of impairment of said mean value as result of failure of a light transmission or a light reception, the value of a combination unimpaired by such a failure.

8. A method according to claim 1, comprising the additional steps of uniformly amplifying the ambient and respective received light values prior to the sampling and storage thereof, and limiting the peak amplification thereof.

9. A method according to claim 1, where said combinations comprise the ratios of the corrected light values of the various receptions as follows:

$$\frac{\text{Short path of a first reception location}}{\text{Long path of said first reception location}} ; \qquad 1)$$

$$\frac{\text{Short path at the second reception location}}{\text{Long path at the second reception location}} ; \qquad 2)$$

$$\frac{\text{Short path at said first reception location}}{\text{Long path at said second reception location}} ; \qquad 3)$$

and $$\frac{\text{Short path at said second reception location}}{\text{Long path at said first reception location}} ; \qquad 4)$$

each of which, under normal conditions is equal to said geometric means of the four corrected light values, and whereby, regardless of the failure of light transmission at one location or of light reception at one location, one of said ratios will be unimpaired by such failure.

10. In an evaluation apparatus, for use in analyzing suspended solids in a liquid, in which light values are derived from light received by two photodetectors from two light sources with each detector receiving light from a respective light source traversing the liquid involved over a relatively short path and from the other light source over a relatively long path with the short paths being of equal length and the long paths being of equal length, the combination of a plurality of sampling and storing means having their inputs adapted to be connected to said photodetectors for sampling and storing the output valves of each of such photodetectors, timing means operatively connected to said sampling and storing means and adapted to be connected to such light sources for alternately actuating said light sources with intermediate periods of no light actuation, representing ambient light values, and simultaneously actuating a respective sampling and storing means for each detector for the respective periods of light actuation and darkness, means, for the storage means associated with each photodetector, for subtracting the stored respective ambient light values from the values received during light actuations, thus representing for each detector the corrected light values received over such a short path and such a long path, means for effecting a logarithmic conversion of each of the corrected light values, means for inverting the log values representing the longer light paths, means for adding the short path log values and the long path inverted log values to provide values representing respective ratios of each short path value to each of the long path values, and for adding all four log and inverted log values together, means for dividing said four value sum by two to form the geometric mean value of said corrected light values which represent the normal output measurement value of the suspended solids, and means for comparing said mean value with each of the four ratio values for monitoring the operation of the device.

11. In an evaluation device according to claim 10, comprising in further combination logic linking means to which the respective four log and inverted log values are conducted together with the outputs of said comparison means, as well as the geometric mean value at the output of said dividing means, for switching, in the presence of a failure in one of the lamp sources or photodetectors the output from the geometric mean value to a corresponding individual value remaining unchanged by such failure.

12. An evaluation device according to claim 11, comprising in further combination, an amplifier interposed between each photodetector and the associated sampling and storing means, and peak detector means for said amplifiers for limiting the peak amplification thereof, and operative to maintain the two amplifiers at identical simultaneous amplification levels.

13. In an evaluation apparatus, for use in analyzing suspended solids in a liquid, particularly in flowing liquids, the combination of a member adapted to be disposed in the liquid to be analyzed, and having a longitudinally extending channel in the bottom thereof, a pair of light sources operatively disposed at one side of said channel and a pair of photodetectors operatively disposed at the opposite side of said channel, arranged to provide a relatively short light path from each source through liquid in said channel to a corresponding photodetector, and a relatively long light path therefrom through liquid in said channel to the other of such detectors, the respective corresponding light paths being equal in length, a plurality of sampling and storing means having their inputs connected to said photodetectors for sampling and storing the output values of each of such photodetectors, timing means operatively connected to said sampling and storing means and adapted to be connected to such light sources for alternately actuating said light sources with intermediate periods of no light actuation, representing ambient light values, and simultaneously actuating a respective sampling and storing means for each detector for the respective periods of light actuation and darkness, means, for the storage means associated with each photodetector, for subtracting the stored respective ambient light values from the values received during light actuations, thus representing for each detector the corrected light values received over such a short path and such a long path, means for effecting a logarithmic conversion of each of the corrected light values, means for inverting the log values representing the longer light paths, means for adding the short path log values and the long path inverted log values to provide values representing respective ratios of each short path value to each of the long path values, and for adding all four log and inverted log values together, means for dividing said four value sum by two to form the geometric mean value of said corrected light values which represent the normal output measurement value of the suspended solids, and means for comparing said mean value with each of the four ratio values for monitoring the operation of the device.

14. In an evaluation apparatus according to claim 15, comprising in further combination logic linking means to which the respective four log and inverted log values are conducted together with the outputs of said comparison means, as well as the geometric mean value at the output of said dividing means, for switching, in the presence of a failure in one of the lamp sources or photodetectors the output from the geometric mean value to a corresponding individual value remaining unchanged by such failure.

15. An evaluation apparatus according to claim 14, comprising in further combination, an amplifier interposed between each photodetector and the associated sampling and storing means, and peak detector means for said amplifiers for limiting the peak amplification thereof, and operative to maintain the two amplifiers at identical simultaneous amplification levels.

16. An evaluation apparatus according to claim 15, wherein the side walls of said channel are parallel to one another and are provided with respective windows therein for the associated light sources and photodetectors which are disposed therebehind, each photodetector being directly opposite a corresponding light source to provide a relatively short light path directly across said channel at substantially right angles to the longitudinal axis of said channel, and diagonally disposed with respect to the other light source to provide a relatively long light path extending diagonally with respect to said axis.

17. An evaluation apparatus according to claim 16, wherein said member is in the form of a float, having a generally pointed bow end adapted to be headed in upstream direction of liquid flow, with said channel being completely disposed below the liquid line of the float member.

18. An evaluation apparatus according to claim 13, wherein the side walls of said channel are parallel to one another and are provided with respective windows therein for the associated light sources and photodetectors which are disposed therebehind, each photodetector being directly opposite a corresponding light source to provide a relatively short light path directly across said channel at substantially right angles to the longitudinal axis of said channel, and diagonally disposed with respect to the other light source to provide a relatively long light path extending diagonally with respect to said axis.

19. An evaluation apparatus according to claim 18, wherein said member is in the form of a float, having a generally pointed bow end adapted to be headed in upstream direction of liquid flow, with said channel being completely disposed below the liquid line of the float member.

20. In a sensor for use in the analysis of suspended solids, particularly in flowing liquids, the combination of a member adapted to be disposed in the liquid to be analyzed and having a longitudinally extending channel in the bottom thereof, the side walls of said channel being parallel to one another, a pair of light sources operatively disposed in longitudinally spaced relation along said channel at one side thereof, and a pair of photodetectors operatively disposed in longitudinally spaced relation along said channel at the opposite side thereof, said detectors and light sources being disposed in fixed relation with the detectors arranged to directly receive light from either light source, said side walls being provided with respective windows therein for the associated light sources and photodetectors which are disposed therebehind, each photodetector being directly opposite a corresponding light source to provide a relatively short light path directly across said channel at substantially right angles to the longitudinal axis of said channel, and diagonally disposed in longitudinal direction with respect to the other light source to provide a relatively long light path extending diagonally with respect to said axis, the respective corresponding light paths being equal in length.

21. A sensor according to claim 20, wherein said member is in the form of a float, having a generally pointed bow end adapted to be headed in upstream direction of liquid flow, with said channel being aligned with said pointed bow end and completely disposed below the liquid line of the float member, whereby liquid flow in the channel takes place with no material impediment or agitation.

* * * * *